United States Patent [19]

Keller et al.

[11] 4,261,587
[45] Apr. 14, 1981

[54] MECHANICAL CHUCKING DEVICE

[75] Inventors: Güenter Keller, Modautalz; Andreas Pohl, Pfungstadtz; Gerhard Hintz, Ober-Ramstadt; Rudolf Sandner, Biebesheim, all of Fed. Rep. of Germany

[73] Assignee: Firma Carl Schenck AG, Darmstadt, Fed. Rep. of Germany

[21] Appl. No.: 968,473

[22] Filed: Dec. 11, 1978

[30] Foreign Application Priority Data

May 6, 1978 [DE] Fed. Rep. of Germany ....... 2819902

[51] Int. Cl.$^3$ .............................................. B23B 31/16
[52] U.S. Cl. .................................... 279/67; 269/224; 269/241; 269/285; 279/1 L; 279/112
[58] Field of Search ............... 279/1 L, 1 SJ, 1 Q, 279/1 W, 67, 68, 112, 110; 73/856, 860; 269/224, 241, 285

[56] References Cited

U.S. PATENT DOCUMENTS

| 273,976 | 3/1883 | Flather | 279/112 |
|---|---|---|---|
| 677,198 | 6/1901 | Fuchs | 279/67 |
| 2,803,157 | 8/1957 | Seitter | 269/224 X |

FOREIGN PATENT DOCUMENTS

| 435920 | 10/1967 | Switzerland | 279/110 |
| 16515 | of 1899 | United Kingdom | 279/112 |

Primary Examiner—Z. R. Bilinsky
Attorney, Agent, or Firm—W. G. Fasse; D. F. Gould

[57] ABSTRACT

The present mechanical chucking device especially for a testing apparatus, has a friction reducing layer interposed between the clamping members and a base plate and another friction reducing layer interposed between the base plate and securing elements for the clamping members, whereby said clamping members may slide within a given range along the base plate without having to release the securing elements holding said clamping members to the base plate. The clamping members are driven by a spindle movably held in a guide block on the base plate which allows an exact concentric clamping of the sample.

8 Claims, 3 Drawing Figures

MECHANICAL CHUCKING DEVICE

BACKGROUND OF THE INVENTION

The present invention relates to a mechanical chucking device especially suitable for use in a testing apparatus but not limited to such use. Two opposing clamping members for clamping test samples are slidably arranged on a base plate.

Many types of mechanical chucking devices for clamping samples in testing machines are known. For example, wedge chucks and chucks with two clamping plates or clamping members are known wherein the plates or members are drawn toward each other by screw means, whereby the sample is clamped between both clamping members or plates. The clamping plates in this type of chucking device are attached to a base plate by means of flexible straps or bars. The base plate itself is attached to the chuck head of the testing device, for example, with threaded bolts. Since the distance between the two clamping plates is practically constant due to the strap connection, intermediate plates or spacers must be used for samples of varying thickness. Hence, such testing machines are used especially for samples with fixed dimensions. It is not possible to continuously vary the sample dimensions, in other words, sample dimensions can be changed only in fixed increments.

In another known chucking device, the clamping members for clamping the sample are slidably arranged on the base plate and secured to the base plate, for example, by bolts which are guided in slots in the base plate. The sample dimensions may thus be continuously varied, however, the clamping members must be disconnected from the base plate and adjusted anew, when clamping a sample. This operation is involved and time consuming. In addition, special care must be taken if a concentric clamping and an exactly concentric power application to the test sample is to be guaranteed.

OBJECTS OF THE INVENTION

In view of the above it is the aim of this invention to achieve the following objects singly or in combination:

to construct a mechanical chucking device for clamping samples in test apparatus which avoids the disadvantages of prior art chucking devices and which is easy to operate;

to provide a chucking or clamping device for test samples which allows a continually varying dimensional change of the sample, in other words, the clamping, spacing, or dimension shall be continuously adjustable;

to provide a chucking device wherein the release of the securing means between the clamping members and the base plate may be avoided when sample dimensions are to be changed, and to provide an apparatus which provides a centered power grip on the test sample.

SUMMARY OF THE INVENTION

The clamping device of the present invention provides a chucking device wherein the clamping members are slidably connected to a base plate by securing means. Sliding improving layers are interposed between the base plate and the clamping members and between the base plate and the securing means. Spindle drive means are arranged on the base plate for guiding, clamping and releasing the clamping members.

The chucking device of the invention has a number of advantages over prior art types of chucking devices. The arrangement of special sliding improving glide surfaces between the clamping members and the base plate and between the securing means and the base plate makes it possible to slide the clamping members on the base plate without necessarily releasing the securing means by which the clamping members are attached to the base plate prior to moving the clamping members. The glide surfaces have very low frictional coefficients, which makes it possible to move the clamping members without releasing the securing bolts, for example, even where the clamping forces required to secure the clamping members to the base plate, are those necessary during tension tests.

By arranging a spindle on the base plate, it is possible to easily clamp the test sample in a centered manner so that an off-center power application to the sample will be avoided. An additional advantage results from the fact that in the most simple case a single clamping means, namely the spindle, is sufficient to clamp the test sample between the clamping members and simultaneously to accomplish a centered guiding of the clamping members.

Another embodiment of the invention provides a guide means for the clamping members for the centered clamping of samples. The guide means are easy to manufacture and result in a simple construction of the chucking device and hence low manufacturing costs.

A further advantageous embodiment of the invention is seen in that additional clamping bolts are provided in addition to the spindle for clamping the sample to the clamping members. The clamping force and thus the transferrable testing force may thereby be considerably increased. Another advantageous embodiment of the invention results, if the spindle and/or the additional clamping bolts act through springs on the clamping members, wherein the springs are suitably cup or Belleville springs or banks of such springs. Through this embodiment of the invention it is possible to maintain during the testing the clamping force substantially constant at the clamping point even where considerable cross-sectional changes of the sample are to be taken into account. By using Belleville springs, high spring strengths may be produced in a small space.

BRIEF FIGURE DESCRIPTION

In order that the invention may be clearly understood, it will now be described by way of example, with reference to the accompaying drawings, wherein.

DETAILED DESCRIPTION OF PREFERRED EXAMPLE EMBODIMENTS AND OF THE BEST MODE OF THE INVENTION

A testing apparatus is usually equipped with two chucking devices attached to the chuck holding heads of the testing apparatus. In the following text the chucking device will simply be referred to as "chuck". The sample is taken up at its both ends by the chucks and clamped tight. One of the two chucks is generally connected to the load application means of the testing apparatus, whereas the other chuck is secured to a rigid part of the apparatus, e.g., the frame. A device for measuring force is usually interposed between the sample and the force application of force take-up. The desired loading of a sample to be tested is transmitted from the testing apparatus to the sample by the chucks.

Figure 1:
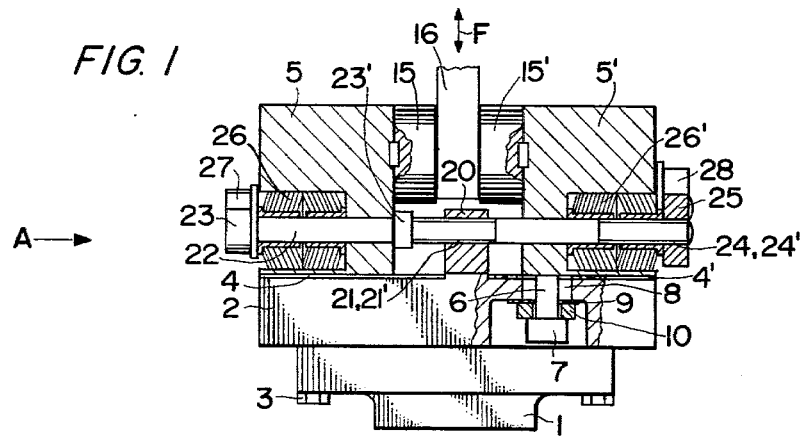
FIG. 1 shows a front view of a mechanical chucking device partially in section.

The chuck of FIG. 1 is attached to the frame or to the loading device 1 of a testing apparatus (not shown). Base means such as a plate 2, which may be rectangular, for example, is attached by appropriate means, e.g., by bolts 3, to the loading device 1. Centering means, not shown, may be provided for the base plate.

The slide improving layers are suitably synthetic films to form glide surfaces, for example, polyimides or polytetrafluoroethelene (PTFE), may be used for these glide surfaces which may be secured to the base plate or to the clamping members or to the securing means for the clamping members. Such films have particularly favorable frictional characteristics under high contact pressure forces.

Preferably the synthetic glide surface 4, 4' is applied to the base plate 2. The just mentioned synthetics are suitable. However, other suitable synthetics or surface layer materials may also be used, which provide favorable surface conditions and low frictional coefficients.

The clamping members 5, 5' are connected to the base plate 2 through the glide surfaces 4, 4' by the securing screw bolts 6. The number of securing bolts 6 for each clamping member depends on the size of the forces to be transmitted through the chuck. Clamping jaws 15, 15' are arranged on the clamping members 5,5'. The clamping jaws 15, 15' grip and clamp the test sample 16. However, the clamping members 5, 5' may directly contact the test sample 16 if desired. After the clamping of the sample 16 in the chuck, test forces indicated by the double arrow F may be applied to the sample 16.

The securing bolts 6 are guided in elongated slots 8 of the base plate 2 whereby the bolts 6 are able to move along with the clamping members 5, 5' in the transverse direction when the clamping members are displaced. The contact surfaces on the base plate 2 for the bolt heads 7 are also provided with a glide surface layer 9 for improving the sliding of the bolt heads 7, which are thus able to slide on the base plate 2 just as easily as the clamping members 5, 5' when the latter are displaced across the base plate 2. Supporting washers 10 may be arranged between the bolt heads 7 and the sliding improving layer 9. The number of securing screw bolts 6 on a chuck, and the biasing forces of the bolts are chosen, so that on the one hand the desired test forces may be transmitted, and on the other hand, transverse movement of the clamping members 5, 5' is possible even if the holding forces of the bolts 6 are effective. Both requirements may be satisfied according to the invention since the glide surfaces 4, 4', 9 have very low friction coefficients. It should also be mentioned, that the glide surfaces may also be arranged on the clamping elements 5, 5' instead of on the base plate 2.

A guiding block 20 is secured to the base plate 2. The guiding block 20 has a female or inner thread 21 forming a guide threading which is engaged by an outer threading 21' of a spindle 22. One end of the spindle 22 has first clamping member engaging elements 23, 23' for the left clamping member 5 in FIG. 1. The engaging element 23 may thus be constructed as a spindle head for adjusting the spindle and may, for example, be provided with a so-called hex socket. The engaging element 23' serves for releasing the clamping and is attached in an appropriate fashion to the spindle threading, for example, by pin means or the like. An additional male threading 24' is provided on the other end of the spindle 22. According to the invention the additional threading 24' has a pitch corresponding to twice the pitch of the guiding thread 21. The threading 24' engages the female threading 24 of a second clamping member engaging element 25 mounted to the clamping member 5'. An exact and automatic centering of the sample 16 in the direction of movement of the clamping members 5, 5' may be realized with this arrangement of the spindle 22 and spindle threading 21' engaging the guide threading 21.

Banks of Belleville or cup spring means 26, 26' are arranged in the clamping members 5, 5'. The spindle 22 extends through said banks of springs 26, 26'. The first engaging element 23 and the second engaging or counter element 25 rest against the spring banks 26, 26'. Hence, the spindle 22 does not act directly on the clamping members 5, 5' but rather through the spring banks 26, 26'. Thus, the clamping power of the chuck remains substantially the same or constant, even when the cross-section of the sample 16 at the clamping point should change during the test. An advantage of this embodiment is seen in that any settling or dimensional change of the sample 16 at the point of clamping, for example, due to transverse strains caused by pressure or tension loading does not have any substantial effect on the secureness of the clamping of the sample since the clamping members 5, 5' are automatically adjusted by the elasticity of the securing and chucking means which hold the sample 16 between the clamping members 5, 5'.

The second engaging or counter element 25 is movably guided at the clamping member 5' so that the element 25 is movable along the spindle axis. For example, the element 25 may be guided at the clamping members 5' by means of pins not shown. The second element 25 may thus follow the compression of the plate springs 26, 26'. When the clamping is released and after the relaxing of the springs or banks of springs, the second element 25 entrains the clamping member 5' via the pins not shown and brings it into the open position. Accordingly, the second element 25 has the same function as the first elements 23, 23' on the other end of the spindle 22.

For small clamping forces the spindle 22 itself is sufficient for clamping the test sample 16. If greater clamping forces are required, further clamping screw bolts 27 may be provided on the clamping members 5, 5', in addition to the spindle 22, for clamping the sample 16. These clamping screw bolts 27 may be connected to the clamping members 5, 5' in similar manner as the spindle 22, namely, through cup springs or spring banks 26", and threaded into counter pieces 28 which are arranged on the clamping members 5 or 5', whereby a common engaging counter piece 28 may be provided for the additional clamping bolts 27 and for the spindle 22. A special guiding of the additional clamping bolts 27 in a guide piece arranged on the base plate is not necessary.

Figure 2:
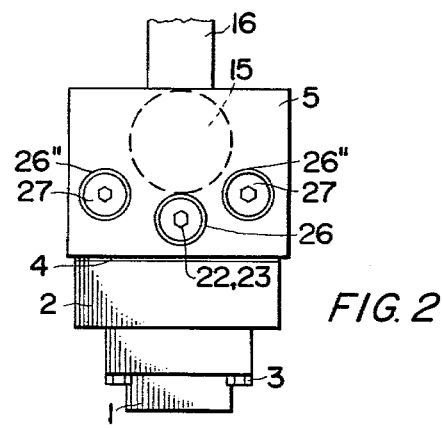
FIG. 2 shows a side view of the device of FIG. 1 as viewed in the direction of the arrow A in FIG. 1.

FIG. 2 shows a side view of the chuck shown in FIG. 1 as viewed in the direction of the arrow A. In this view especially, a possible arrangement of the additional clamping bolts 27 is illustrated. These bolts 27 act on the clamping members 5 or 5' through cup springs or spring banks 26". The reference numbers in FIG. 2 indicate the same elements as in FIG. 1.

Figure 3:
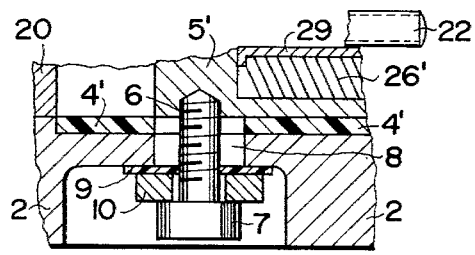
FIG. 3 shows a detail of FIG. 1 on a somewhat enlarged scale.

FIG. 3 shows a somewhat enlarged detail of FIG. 1 to illustrate the location of the sliding improving layer 4' between the base 2 and the clamping member 5'. The layer 4' may be laminated to the member 5' or to the base 2. This applies also to the layer 4. The springs 26' are located in a suitable busing 29 which receives the spindle 22.

The sliding improving layer 9 is interposed between the washer 10 and a shoulder in the base 2, said shoulder surrounds an elongated hole 8 in the base 2 through which a screw bolt 6 extends to secure the clamping member 5' to the base. The layer 9 may be laminated to the base 2 or to the washer 10. In both instances the member 5' may be shifted along the base without releasing the screw bolt 6.

Although the invention has been described with reference to specific example embodiments, it is to be understood that it is intended to cover all modifications and equivalents within the scope of the appended claims.

What is claimed is:

1. A mechanical chucking device for clamping a work piece, such as a test sample, in a centered manner in a material testing machine, comprising base means (2), first and second clamping means (5, 5') operatively arranged to be slidable on said base means toward and away from each other, securing means (6, 7, 8) for movably securing said first and second clamping means (5, 5') to said base means, a single threaded spindle, threaded spindle guide means (20, 21) secured to said base means (2) intermediate said first and second clamping means, said single threaded spindle extending through said threaded spindle guide means for operatively connecting said single threaded spindle to said base means (2) intermediate said first and second clamping means, said threaded spindle guide means having a given threading pitch, said first and second clamping means comprising first and second clamping members, said single threaded spindle extending operatively and rotatably through said first and second clamping members without direct engagement between the spindle and the clamping members, one threaded end of said single threaded spindle having a threading with a pitch corresponding to twice said given threading pitch of said threaded spindle guide means, counter nut means (25) engaging said threaded spindle end, and wherein the other end of said single threaded spindle comprises means (23, 23') for engaging the other clamping member for moving said first and second clamping members along said base means relative to each other, first sliding improving means (4, 4') operatively interposed between said base means (2) and said first and second clamping means (5, 5'), and second sliding improving means (9) operatively interposed between said base means (2) and said securing means (6, 7, 8).

2. The chucking device of claim 1, wherein said first and second sliding improving means are secured to said base means.

3. The chucking device of claim 1, wherein said first sliding improving means (4, 4') are secured to said clamping members, wherein said second sliding improving means (9) are secured to said base means (2), and wherein said first and second sliding improving means are made of a synthetic material.

4. The chucking device of claim 1, further comprising threaded clamping bolt means (27) operatively connected to said clamping means (5, 5') for supplying an additional clamping force for clamping the test sample (16).

5. The chucking device of claim 4, further comprising spring means (26") operatively arranged between said clamping members and said threaded clamping bolt means (27).

6. The chucking device of claim 1, further comprising spring means (26, 26') operatively arranged between said single threaded spindle and said clamping members.

7. The chucking device of claim 5 or 6, wherein said spring means comprise cup spring means.

8. A mechanical chucking device for clamping a test sample in a centered manner without play in a material testing machine comprising a base (2), a first clamping member and a second clamping member slidable on said base toward and away from each other, a spindle guide member (20) rigidly secured to said base between said first and second clamping members, said spindle guide member having a threaded bore (21') therethrough for permitting an axial spindle movement, securing means for movably securing said first and second clamping members to said base, a single threaded spindle having a central threaded portion, a smooth spindle end and a threaded spindle end, said central threaded spindle portion operatively engaging said threaded bore of said spindle guide member, said smooth spindle end being rotatably connected to one of said clamping members, said threaded spindle end extending rotatably through said other clamping member, a counter nut operatively engaging said threaded spindle end and said other clamping member for moving said first and second clamping members by rotating said single threaded spindle, sliding improving means operatively interposed between said base and said clamping members and between said base and said securing means, and cup spring means between each end of said threaded spindle and the respective clamping member for taking up play.

* * * * *